(12) United States Patent
Hallauer et al.

(10) Patent No.: US 12,313,210 B2
(45) Date of Patent: May 27, 2025

(54) SYSTEM FOR JOINING A DEVICE, IN PARTICULAR A MEDICAL DEVICE, TO A SUPPORT

(71) Applicant: AXESS VISION TECHNOLOGY, Joue-les-Tours (FR)

(72) Inventors: Emmanuel Hallauer, Sache (FR); Philippe Le Roux, Tours (FR)

( * ) Notice: Subject to any disclaimer, the term of this patent is extended or adjusted under 35 U.S.C. 154(b) by 433 days.

(21) Appl. No.: 17/793,068

(22) PCT Filed: Jan. 12, 2021

(86) PCT No.: PCT/FR2021/050051
§ 371 (c)(1),
(2) Date: Jul. 15, 2022

(87) PCT Pub. No.: WO2021/144530
PCT Pub. Date: Jul. 22, 2021

(65) Prior Publication Data
US 2023/0040194 A1  Feb. 9, 2023

(30) Foreign Application Priority Data
Jan. 17, 2020 (FR) ...................................... 2000448

(51) Int. Cl.
*F16M 11/04* (2006.01)
*F16M 13/02* (2006.01)

(52) U.S. Cl.
CPC ........... *F16M 11/041* (2013.01); *F16M 11/04* (2013.01); *F16M 13/02* (2013.01)

(58) Field of Classification Search
CPC ...... F16M 11/041; F16M 11/04; F16M 13/02; A61B 1/00131; A61B 90/50
See application file for complete search history.

(56) References Cited

U.S. PATENT DOCUMENTS

| | | | | |
|---|---|---|---|---|
| 2,283,974 | A * | 5/1942 | Dillon | F16L 37/252 285/332.1 |
| 5,114,060 | A * | 5/1992 | Boyer | B62J 11/00 224/431 |
| 9,243,739 | B2 * | 1/2016 | Peters | A45F 5/00 |
| 10,550,992 | B2 * | 2/2020 | Yun | B60R 11/0241 |
| 2008/0315049 | A1 | 12/2008 | Bailo et al. | |

(Continued)

FOREIGN PATENT DOCUMENTS

| | | |
|---|---|---|
| EP | 2803585 A1 | 11/2014 |
| EP | 3029543 A1 | 6/2016 |
| WO | 2018204937 A2 | 11/2018 |

*Primary Examiner* — Anita M King
(74) *Attorney, Agent, or Firm* — Jonathan Bingham (57) ABSTRACT

This disclosure relates to a removable system for joining a device to a support, using a male part interacting with a female part;
the male part including an arm having a free end provided with a series of bearing teeth extending radially;
the female part including at least one locking plate in which is arranged an opening delimiting retaining teeth able to come face-to-face with a bearing tooth to prevent the disengagement between the male and female parts;
the female part and the male part including an angular locking device able to angularly lock the female and male parts, the angular locking device including a latch mounted radially movable on the back face of the locking plate.

14 Claims, 4 Drawing Sheets

(56) References Cited

U.S. PATENT DOCUMENTS

| | | | |
|---|---|---|---|
| 2014/0339385 A1* | 11/2014 | Boer | B64D 47/00 |
| | | | 248/222.52 |
| 2014/0360893 A1 | 12/2014 | Whitten et al. | |
| 2015/0136933 A1 | 5/2015 | Merzon | |
| 2019/0154190 A1 | 5/2019 | Yun | |
| 2020/0085530 A1* | 3/2020 | Sauer | A61B 17/06061 |
| 2020/0132244 A1* | 4/2020 | Yun | B62J 11/00 |

* cited by examiner

SYSTEM FOR JOINING A DEVICE, IN PARTICULAR A MEDICAL DEVICE, TO A SUPPORT

TECHNICAL FIELD

This disclosure relates to the technical field of attachment systems used to temporarily secure on a support, an electronic device in the general sense.

This disclosure finds applications in many industrial fields but it is more particularly aimed at the medical field where an electronic medical device is to be temporarily attached to a support, such as an intravenous stand or intravenous pole for example.

The subject of the disclosure has a particularly advantageous application in the field where the electronic medical device is a display screen used with a medical device, such as an endoscope, this screen being intended to be temporarily suspended during the use of the endoscope.

A medical endoscope in the general sense is used to access the inside of a hollow organ, a cavity or natural or artificial conduit of the human body in order to perform various operations for therapeutic, surgical or diagnostic purposes.

BACKGROUND

In general, an endoscope includes a control handle taking the form of a casing adapted to be held by a user of the endoscope and to which a tubular structure designed to be inserted into a body cavity of a patient to be examined, is fixed. This tubular insertion structure includes a distal head equipped with a vision system that allows illuminating and examining the organ, cavity or the conduit of the human body. Upstream of the distal head, the tubular insertion structure includes an angulation part controlled by a mechanism of the control handle to orient the distal head inside the insertion channel. To view the inside of the hollow organ, cavity or the conduit of the human body into which the endoscope is inserted, the endoscope is connected to a display screen on which the images coming from the vision system are displayed.

Fixed viewing screens are very widespread: these are screens attached to the wall of the operating theater for example. The stability of these screens is then guaranteed. However, in order to perform an endoscopy, it is then essential to be in a room equipped with a fixed display screen. In a hospital or clinic, this requires either to equip all the rooms with display screens, or to limit the performing of endoscopies to certain rooms. This is why it is advantageous to be able to have a movable display screen.

Movable display screens are also known. These are in particular standing screens, which can be set down on a support surface present in the operating room. According to the dimensions and the weight of these screens, their movement is not always easy.

There is in particular the movable display screen marketed by AMBU® under the name AVIEW™, which is movable and of small bulk. This display screen has the advantage not only of being able to be set down on an installation plane, but also to be able to be attached to an intravenous pole. For this purpose, the display screen includes on its back face a screw attachment system including a hoop, one of the arms of which is provided with a screw, which when tightened onto the intravenous pole makes it possible to suspend the screen while being able to adjust its position with respect to the pole. To make the screen easily detachable with respect to the screw attachment system, the back of the screen is provided with a slider intended to interact with a complementary slider arranged on the screw attachment system. In practice it proves that the mounting and removal of the screen are relatively difficult operations to perform properly since they require the perfect alignment of the slider of the back of the screen with the slider of the support. Beyond these manipulation problems, the mounting and removing operations are accompanied by a considerable risk of dropping the screen and consequently damaging the screen.

There is also known from the patent application US 2019/154190, a system for mounting an electronic device on a vehicle. This attachment system includes an attachment part secured to the electronic device and including protrusions and grooves disposed alternately. This system also includes a locking cap provided with a protrusion and a rotary cap having a groove and mounted rotatable with respect to the locking cap. The support is attached to the attachment part by inserting the protrusion of the locking cap into a groove of the attaching part and by relatively turning the attaching part with respect to the locking cap. During this rotation, a tab of a locking member cooperates with the groove of the rotary cap, preventing the withdrawal of the locking cap with respect to the attaching part. Such an attachment system has a relatively complex and cumbersome design with a locking member protruding from the electronic device to be actuated.

The patent application US 2014/360893 relates to a device for mounting a protection shell of a portable electronic device on a support. This protective shell includes in its rear wall, a housing delimited by spaced teeth and into which is inserted a locking element provided with tabs which after rotation are locked behind the teeth of the protective shell. Such a device also has the drawback that the unlocking element projects protrudes from the electronic device in order to be actuated.

The patent application US 2015/136933 describes a connection system for removably mounting a portable electronic device on a flat surface. This system includes a male connector provided with teeth intended to engage in a female connector having housings of a shape complementing that of the teeth. A relative rotation of the male connector with respect to the female connector allows them to be secured together. However, such a connection system does not ensure a secure immobilization and a rotational immobilization of the portable electronic device with respect to the flat surface.

SUMMARY

The present disclosure therefore aims to overcome the drawbacks of the state of the art by proposing a new removable joining system designed to allow the easy mounting and dismounting of a device on a support, these mounting and dismounting operations being able to be performed in total safety for the device.

This disclosure also aims to propose a new removable joining system designed to allow, with a single hand, the mounting and dismounting of a device on a support.

To achieve such an aim, the system according to the disclosure aims to provide the removable joining of a device to a support, using a male part equipping the support and interacting with a female part equipping the device:

the male part including an arm having a free end provided with a series of bearing teeth extending radially in a radial plane being distributed over an angular distribution;

the female part including at least one locking plate delimited by a front face and a back face and in which is arranged an opening of a section suitable for allowing, in an insertion position, the engagement, from the front face, of the free end of the male part beyond the back face, the opening arranged in the locking plate delimiting retaining teeth extending radially and which, after a relative rotation between the female part and the male part, are able, in a locking position, to come face-to-face with a bearing tooth to prevent the disengagement, between the male and female parts, of the back face in the direction of the front face;

the female part and the male part including an angular locking device able to angularly lock the female and male parts when they are occupying the locking position, the angular locking device including a latch mounted radially movable on the back face of the locking plate and provided with a translating member accessible from the front face of the locking plate, the latch being intended to automatically engage in a limiting groove of the external edge of a bearing tooth;

the female part including an abutment bottom for the male part limiting the engagement of the male part beyond the back face of the locking plate and having a rotational guiding surface between the male part and the female part in order to change from the insertion position to the locking position and conversely.

In addition, the system according to the disclosure can further include in combination at least one and/or the other of the following additional features:

the abutment bottom includes, as a rotational guiding surface, a circular stud of conical shape;

the male part includes a number of bearing teeth equal to the number of retaining teeth of the female part;

the bearing teeth of the male part and the retaining teeth of the female part are regularly angularly distributed;

two neighboring retaining teeth of the female part together delimit a notch for passing a bearing tooth of the male part while two neighboring bearing teeth of the male part together delimit a hole for passing a retaining tooth of the female part;

the angular width of a passing notch measured between two neighboring retaining teeth is equal to a value between 105 to 200% of the angular width measured for a bearing tooth;

the external edge of the bearing teeth includes from each of its ends a bearing rail for the latch opening into a limiting groove for the latch;

the latch is elastically stressed in extension by a spring member in its maximum extension position in such a way as to be gradually compressed when it is bearing against the rail of the external edge until it comes to automatically engage in the limiting groove;

the latch is intended to automatically engage in a limiting groove of the external edge of a bearing tooth under the effect of its own weight;

the latch is mounted to extend vertically plumb with the middle of a retaining tooth arranged in the locking plate.

Another subject of the disclosure is to propose an equipment including a device assembled with a support using a removable joining system in accordance with the disclosure.

According to an advantageous variant embodiment, the device includes a casing with a back face provided with the female part of the joining system, the male part of which equips the support. Advantageously, the back face of the casing of the device is provided with the translating member of the locking latch, positioned in the vicinity of the upper edge of the casing.

In a preferred application, the device is a display screen of a medical endoscope.

Various other features emerge from the description given below with reference to the appended drawings which show, by way of non-limiting example, forms of embodiment of the subject of the disclosure.

DETAILED DESCRIPTION

The subject of the disclosure relates to a removable joining system 1 for providing the dismountable joining of a device 2 to a support 3 of any type known per se. In a preferred application, the support 3 is from the medical field. By way of example, the support 3 can be a medical accessory commonly known as an intravenous stand or an intravenous pole. Of course, the support 3 can be embodied differently in the form of an item of furniture or a trolley. The support 3 is schematized in the drawings in the form of a cylindrical body solely by way of illustration.

The removable joining system 1 in accordance with the disclosure allows to temporarily hooked onto the support 3, a device 2 of any type. According to a preferred example of application, the removable joining system 1 allows the hooking, of a medical electronic device such as a medical monitor or advantageously, a display screen 2 intended to be connected to a medical endoscope of any type known per se. This display screen 2 can thus be attached temporarily to the support 3 (intravenous stand or intravenous pole for example) particularly during the use of the medical endoscope to which the display screen 2 is attached.

As shown more specifically in FIGS. 1 to 8, the removable joining system 1 includes two independent parts namely a male part I and a female part II intended to interact together to allow the attachment of the device 2 on the support 3. In the exemplary embodiment illustrated in the drawings, the device 2 is provided with the female part II while the support 3 is fitted with the male part I. Of course, provision can be made for another variant embodiment for which the device 2 is provided with the male part I while the support 3 is fitted with the female part II.

Figure 4:
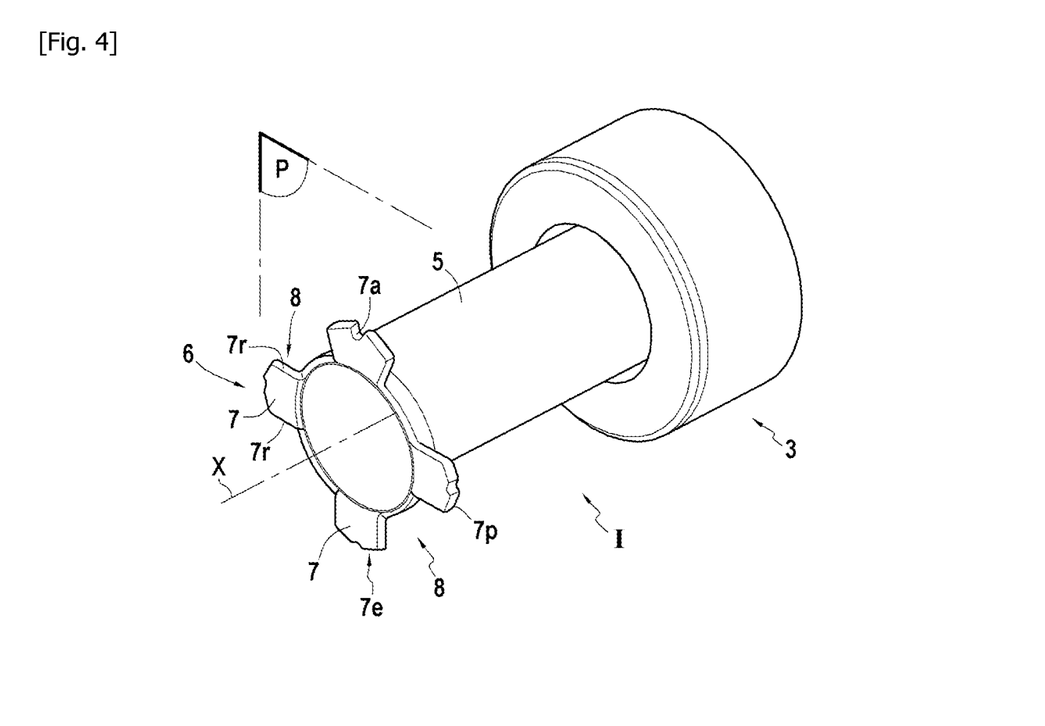
FIG. 4 is a perspective view of the male part of the removable joining system in accordance with the disclosure.

As shown more specifically in FIG. 4, the male part I includes an arm 5 having a free end 6 and extending longitudinally along a longitudinal axis which will be called axis of insertion X in the rest of the description. The free end 6 of the arm 5 is provided with a series of bearing teeth 7 extending perpendicularly with respect to the axis of insertion X. The bearing teeth 7 extend radially in a radial plane P perpendicular to the axis of insertion X. In the example illustrated on the drawings, the arm 5 has a tubular shape of circular section but it is clear that the arm 5 can have a different shape.

The bearing teeth 7 are distributed on the periphery of the arm 5 in a determined angular distribution, preferably even. According to the illustrated example, the arm 5 is equipped with four bearing teeth 7 angularly offset pairwise by 90°. It is clear that the number of bearing teeth 7 can be different from four and can be between 2 and 10 for example. Two neighboring bearing teeth 7 together delimit a passage hole 8. In the illustrated example, the free end of the arm 6 includes four bearing teeth 7 delimiting four passing holes 8.

The angular width of the bearing teeth 7 can take different values suitable for enabling the bearing teeth 7 to provide their locking function as it will be better understood in the remainder of the description. Preferably but not exclusively, the angular width is identical for all the bearing teeth 7. For example, the angular width of a bearing tooth 7 is equal to a value between 0.5 to 0.9 times the angular width of a passing hole 8.

Each bearing tooth 7 is delimited by an external edge 7e. Each bearing tooth 7 can be of any shape. In the illustrated example, each bearing tooth 7 is of substantially rectangular shape. According to this example, the external edge 7e of each bearing tooth 7 includes on either side two radial parts 7r interconnected by a peripheral part 7p.

According to an advantageous variant embodiment, the peripheral part 7p of the external edge 7e includes from each radial part 7r, a bearing rail, the height of which in relation to the arm 5 increases in the direction of the median part of the peripheral part 7p. The two bearing ramps meet in the middle of the peripheral part 7p of the external edge 7e, at the level of a limiting groove 7a the function of which will appear more precisely in the remainder of the description.

The female part II includes at least one locking plate for example taking the form of a locking disk 10 delimited by a front face 11 and a back face 12, and in which is arranged an opening 13 of a section suitable for allowing, in an insertion position, the engagement, from the front face 11, of the free end 6 of the male part II beyond the back face 12. The front 11 and back 12 faces are determined by considering the position of the male part I with respect to the female part II, before the insertion of the male part I into the female part II.

In other words, the front face 11 corresponds to the face directed outward such that the external face of the back wall of the device 2 in the illustrated example while the back face 12 corresponds to the internal face of the rear wall of the device 2. The insertion of the male part I in the female part II is embodied by a relative displacement along the axis of insertion X, between the male part I and the female part II. To obtain this insertion, the male part is displaced with respect to the female part, the female part is moved with respect to the male part or the male part and the female part are moved simultaneously.

Figure 5:
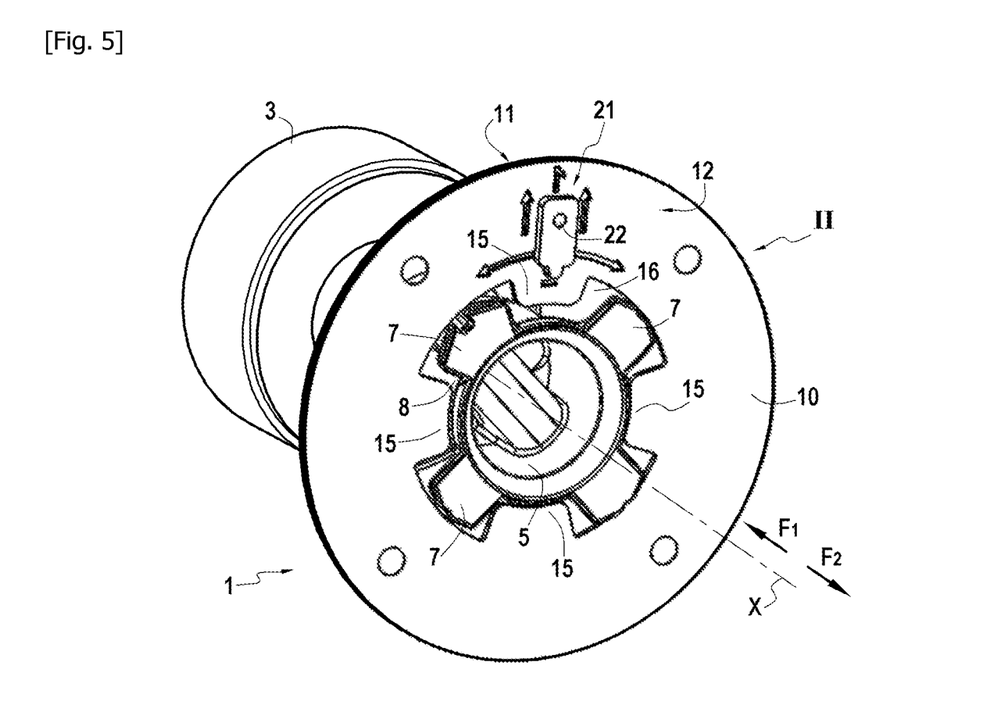
FIG. 5 is a perspective view showing the engagement of the male part in the female part of the removable joining system in accordance with the disclosure.

By way of example in the remainder of the description, the direction of engagement is denoted by the arrow F1 and corresponds to the displacement of the female part II to obtain the insertion of the male part I into the female part II, from the front face 11 of the female part (FIG. 5). Conversely, the direction of disengagement is denoted by the arrow F2 and corresponds to the displacement of the female part II to obtain withdrawal of the female part II with respect to the male part, in a direction contrary to the direction of engagement F1.

To allow the insertion of the male part into the female part, it should be understood that the passing section of the opening 13 of the locking disk 10 is greater than the section of the free end 6 of the male part II, taken in the radial plane and formed by the section of the arm 5 and by the section or the surface of the bearing teeth 7. In other words, the section of the free end 6 of the male part II taken in the radial plane comprising the arm 5 and the bearing teeth 7 is strictly contained in the passing section of the opening 13.

Figure 1:
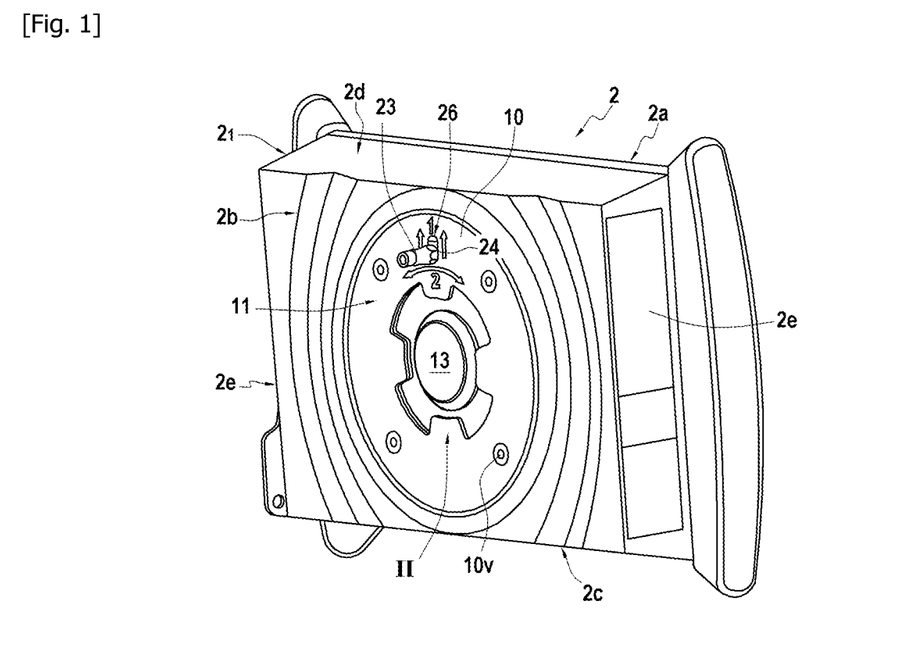
FIG. 1 is a rear three-quarter perspective view of a medical device embodied in the form of a display screen equipped with the female part of the removable joining system in accordance with the disclosure.
Figure 2:
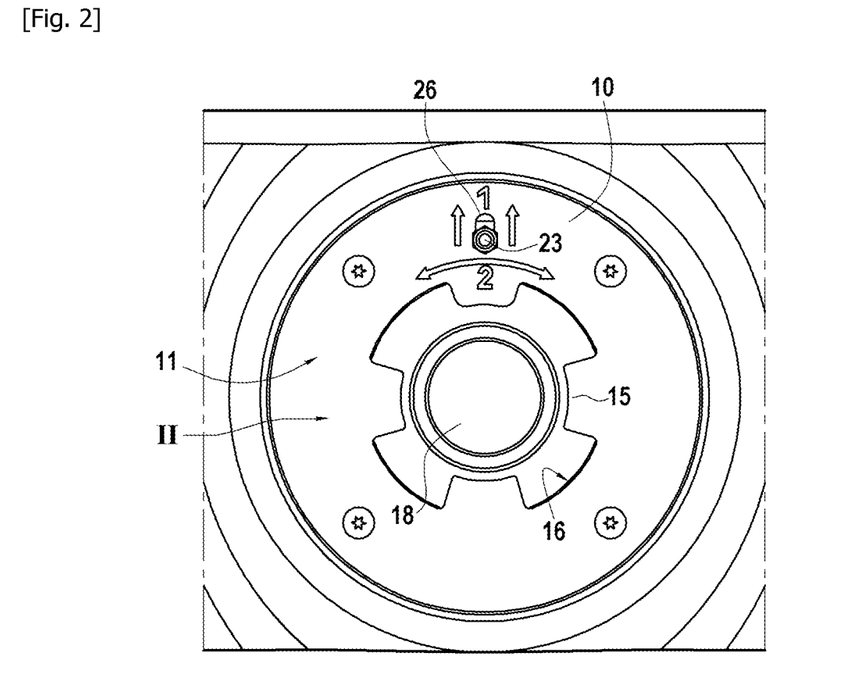
FIG. 2 is a back view of the medical device illustrated in FIG. 1.
Figure 3:
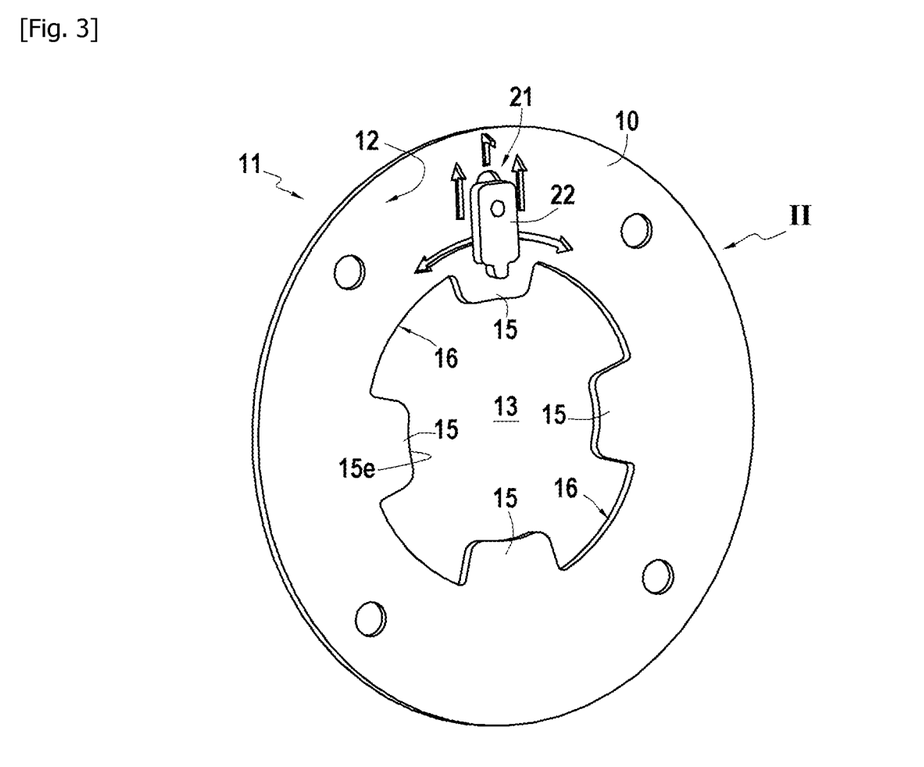
FIG. 3 is a rear view of the back of the medical device illustrated in FIG. 2.

The opening 13 is arranged in the disk 10 to delimit retaining teeth 15 extending radially (FIG. 3). The retaining teeth 15 are distributed about a circumference of the disk 10 with a given angular distribution, preferably regular. According to the illustrated example, the disk 10 is equipped with four retaining teeth 15 angularly offset pairwise by 90°. It is clear that the number of retaining teeth 15 may be different from four and can be, for example, between 2 and 10. According to the exemplary embodiment, the female part II includes a number of retaining teeth 15 equal to the number of bearing teeth 7 of the male part I. Of course, the number of retaining teeth 15 can be different from the number of bearing teeth 7 of the male part I.

Each retaining tooth 15 is delimited by an external edge 15e. Each retaining tooth 15 can have any shape. In the illustrated example, each retaining tooth 15 has a substantially rectangular shape. Two neighboring retaining teeth 15 together delimit a passing notch 16 for a bearing tooth 7 of the male part I. According to an advantageous embodiment feature, the angular width of a notch 16 measured between two neighboring retaining teeth 15 is equal to a value between 105 to 200% of the angular width of a bearing tooth 7.

Thus, upon the engagement of the male part I in the female part II along the axis of insertion X, the distal end 6 is able to cross the opening 13. Thus, the bearing teeth 7 cross the opening 13 via the notches 16 while the holes 8 allow for the passing of the retaining teeth 15. The bearing teeth 7 can thus extend beyond or behind the back face 12 of the locking disk 10 in such a way as to allow the relative rotation between the male part I and the female part II about the axis of insertion X. Of course, the female part II delimits, from the back face 12 of the locking disk 10, a disengagement allowing the positioning and the rotation of the free end 6 of the arm 5 provided with bearing teeth 7.

Figure 6:
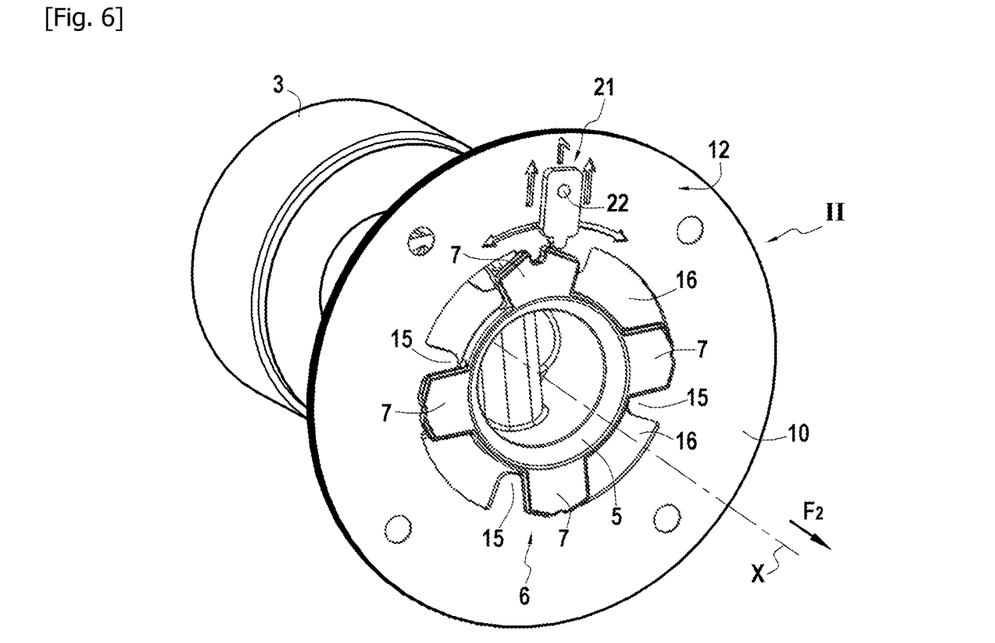
FIG. 6 is a perspective view after the engagement of the male part in the female part of the removable joining system in accordance with the disclosure, the position of the female part with respect to the male part after a relative rotation.

The retaining teeth 15 are arranged in such a way that after a relative rotation between the female part II and the male part I, at least one and preferably all of the bearing teeth 7 are able to be positioned at least partly face-to-face with the retaining teeth 15 to prevent the disengagement, between the male parts I and female parts II, along the direction of disengagement F2 opposite to the direction of insertion F1 (FIG. 6). According to the preferred exemplary embodiment illustrated on the drawings, each retaining tooth 15 is locked by a bearing tooth 7 for a displacement of the female part II in the direction of disengagement F2. When the male part I and the female part II occupy this position, the removable joining system 1 is in a position of translational locking.

According to an advantageous embodiment feature, the female part II includes an abutment bottom 18 for the male part I limiting the engagement of the male part beyond the back face 12 of the locking disk 10. This abutment bottom 18 is positioned to allow the positioning of the bearing teeth 7 behind the retaining teeth 15 while remaining in contact with or bearing on these latters. This abutment bottom 18 can exert a bearing force in the opposite direction to the direction of insertion to provide a bearing for the bearing teeth 7 against the retaining teeth 15. This abutment bottom 18 has a compressive ability due to its constituent material or is stressed, by a spring member for example.

Advantageously, the abutment bottom 18 has a rotational guiding surface between the male part I and the female part II in order to allow the change from the insertion position to the locking position and conversely. For example, the abutment bottom 18 is embodied by a circular stud of conical shape on which the distal end of the tubular arm 5 bears, favoring the rotational guiding and the centering on approach of the two parts, namely the male part and the female part.

According to another aspect of the disclosure, the female part II and the male part I include an angular locking device 21 able to angularly lock the female II and male I parts when they are occupying the locking position. According to the exemplary embodiment illustrated in the Figures, the angular locking device 21 includes a latch 22 mounted radially movable on the back face 12 of the locking disk 10. Advantageously, this latch 22 is mounted to extend vertically, plumb with the middle of a retaining tooth 15 and preferably, the retaining tooth 15 located at the highest level vertically. As shown in the figures, the latch 22 extends radially back from the internal edge delimited by the opening 13 and in particular by a retaining tooth 15 and also back from the external edge of the locking disk 10 such that the latch 22 is totally invisible from the front face 11 of the locking disk 10.

This latch 22 is provided with a member 23 making it possible to translationally move it and positioned to be accessible from the front face 11 of the locking disk 10. For this purpose, the latch 22 is provided with a stem 24 connected to the displacement member 23 protruding with respect to the front face 11. The stem 24 crosses an oblong aperture 26 made in the locking disk 10 to allow the radial displacement of the latch 22. The latch 22 is intended to interact by its terminal part with a bearing tooth 7 to ensure the rotational locking of the male part I with respect to the female part II. As it will be explained in the remainder of this description, the displacement member 23 is intended to be displaced to unlock the rotational locking.

Figure 7:
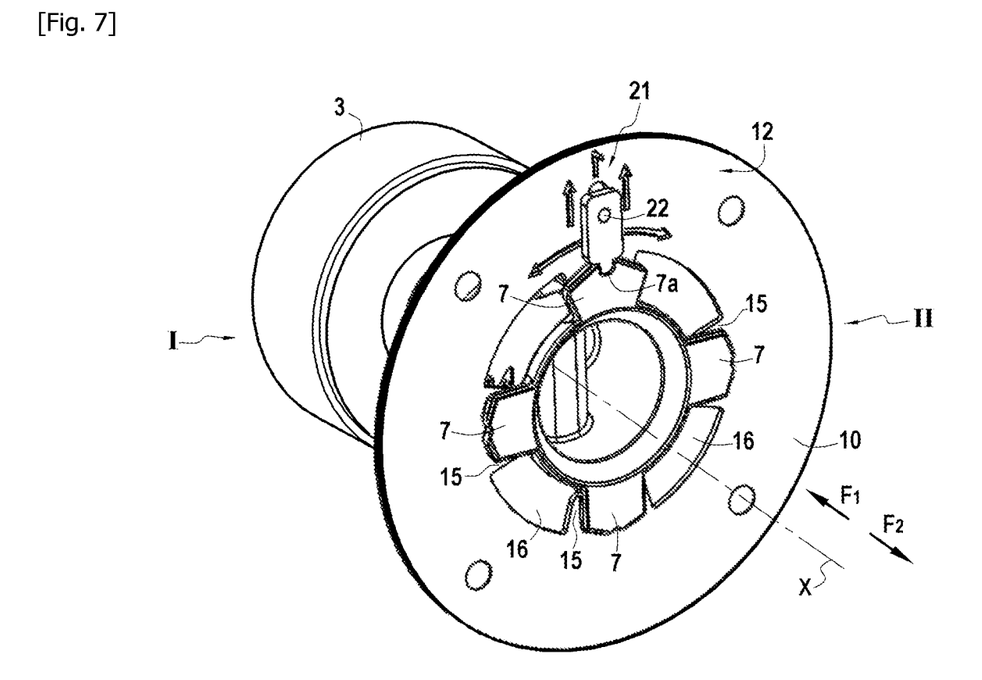
FIG. 7 is a perspective view showing the locking of the male part in the female part of the removable joining system in accordance with the disclosure.

According to the exemplary embodiment illustrated, the latch 22 is intended to engage in the limiting groove 7a of the bearing tooth located in correspondence. During the relative rotation between the male and female parts, the latch 22 is in contact with the external edge 7e of a bearing tooth 7 and then engages in the limiting groove 7a to lock the rotation (FIG. 7). The latch 22 automatically engages in the limiting groove 7a under the effect of its weight or the latch 22 is elastically stressed by a spring member in its maximal extension position in such a way as to be gradually compressed when it is bearing on the rail of the external edge 7e until it automatically engages in the limiting groove 7a. The angular locking is done automatically during the relative rotation between the male and female parts.

Figure 8:
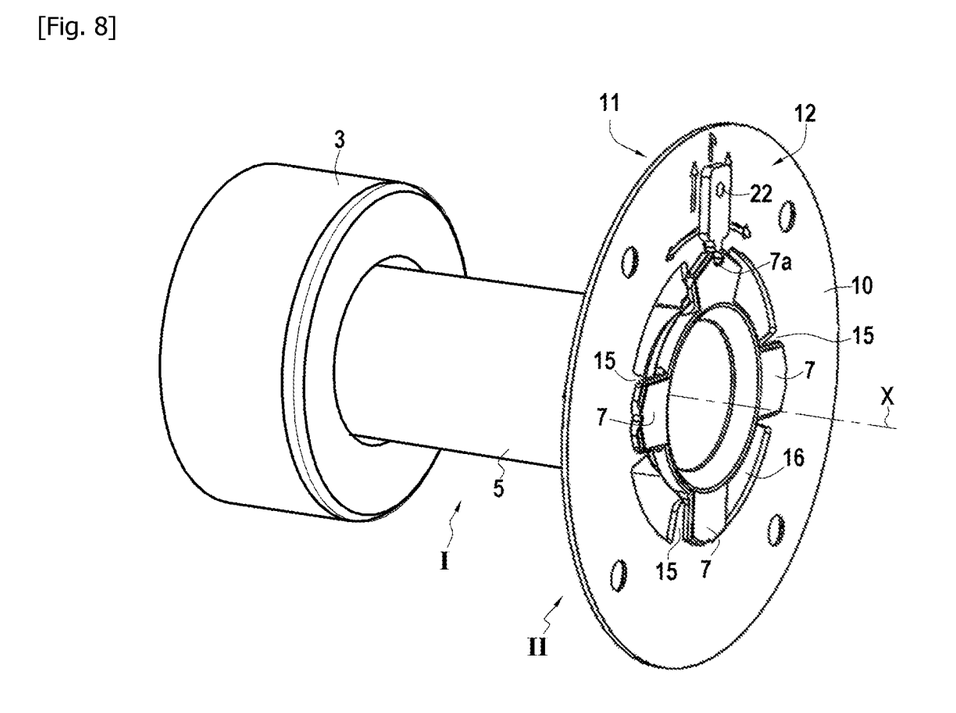
FIG. 8 is a perspective view showing the first phase of unlocking of the male part with respect to the female part of the removable joining system in accordance with the disclosure.

Of course, the rotational unlocking of the male part I with respect to the female part II consists in lifting the actuating member 23 to disengage the latch 22 from the limiting groove 7a (FIG. 8). It then becomes possible to turn relatively the female and male parts in relation to one another.

According to the exemplary embodiment illustrated, the latch 22 includes a protruding end part intended to engage in a limiting groove 7a. Of course, the latch 22 can have an end part embodied with a different shape such as for example the shape of a claw which then engages on either side of a bead carried by the bearing tooth 7. Moreover, the angular locking device 21 can be different from a latch acting radially and vertically on a bearing tooth 7. Thus, the angular locking device 21 can be embodied, for example, by a latch acting axially to engage in a hole arranged in the bearing tooth 7 placed in correspondence.

The implementation of the removable joining system 1 in accordance with the disclosure follows on directly from the previous description. The joining of the male part I to the female part II consists in positioning the terminal end 6 of the male part in front of the front face 11 of the female part, by aligning the bearing teeth 7 of the male part I with the notches 16 of the female part II (FIG. 5). The relative displacement along the direction of engagement F1 along the axis of insertion X, between the male part I and the female part II, leads the male part I and the female part II to occupy an insertion position in which the bearing teeth 7 extend beyond or behind the back face 12 of the locking disk 10 (FIG. 6). Advantageously, the final insertion position along the axis of insertion X is given by the placing of the terminal part 6 of the male part I in abutment with the abutment bottom 18 of the female part II. The male part I and the female part II are therefore locked along the direction of engagement F1.

In this final insertion position, a relative rotation between the male part I and the female part II leads the latch 22 to come into contact with the external edge of the bearing tooth 7 in correspondence. During this rotation, the latch 22 is gradually lifted by the rail arranged on the external edge 7e and then automatically engages in the groove 7a. In this position, the male part I and the female part II are therefore rotationally locked in relation to one another. Also in this position, the bearing teeth 7 are located face-to-face with the retaining teeth 15 such that the male part I and the female part II are locked along the direction of disengagement F2. In the position illustrated in FIG. 7, the male part I and the female part II are joined together by a full coupling by the system in accordance with the disclosure.

The separation between the male part I and the female part II is made by performing the reverse operations to those described previously. The latch 22 is lifted using the displacement member 23 accessible from the front face 11, to disengage it from the bearing tooth 7 (FIG. 8) allowing the relative rotation between the male part I and the female part II until the bearing teeth 7 become positioned face-to-face with the notches 16. The relative displacement along the direction of disengagement F2 along the axis of insertion X, between the male part I and the female part II, leads the male part I and the female part II to occupy a disengagement position wherein the bearing teeth 7 extend beyond or in front of the front face 11 of the locking disk.

The removable joining system 1 in accordance with the disclosure makes it possible to ensure the dismountable joining of a device 2 on a support 3 of any type known per se. In a preferred application, the support 3 is from the medical field while the device 2 is a display screen intended to be connected to a medical endoscope of any type known per se. According to the illustrated example in FIG. 1, the display screen 2 is equipped with the female part II. For this purpose, the display screen 2 includes a casing 21 having a front face 2a and a back face 2b extending substantially face-to-face with the front face 2a. The casing comprises a lower edge 2c and opposite it an upper edge 2d. This lower edge 2c and the upper edge 2d are interconnected by two lateral edges 2e. A part of the back face 2b is provided with the locking plate 10 with its front face turned toward the outside of the casing while the abutment bottom 18 is mounted inside the casing. The locking plate 10 is for example attached by screws 10v on the back face 2b of the casing. Advantageously, the locking plate 10 is mounted in such a way that the displacement member 23 of the locking latch 22 becomes preferably positioned near the upper edge 2d of the casing. Such a positioning makes it possible to unlock the latch by lifting it and simultaneously pick up the screen with a single hand.

It is apparent from the previous description that the subject of the disclosure also relates to an equipment including a device 2 joined to a support 3 in the general sense using a removable joining system 1 in accordance with the disclosure. The device 2 is equipped for example with the female part II while the support 4 is provided with the male part I. The device 2 can be mounted and dismounted easily with respect to the support 3.

The disclosure is not limited to the examples described and shown since various modifications can be made to it without departing from its scope.

The invention claimed is:

1. A removable system for joining a device to a support, using a male part equipping the support and interacting with a female part equipping the device;
   the male part including an arm having a free end provided with a series of bearing teeth extending radially in a radial plane and distributed over an angular distribution;
   the female part including at least one locking plate delimited by a front face and a back face and in which is arranged an opening of a section suitable for allowing, in an insertion position, the engagement, from the front face, of the free end of the male part beyond the back face, the opening arranged in the locking plate delimiting retaining teeth extending radially and which, after a relative rotation between the female part and the male part, are able, in a locking position, to come face-to-face with a bearing tooth to prevent the disengagement, between the male and female parts, of the back face in the direction of the front face,
   the female part and the male part including an angular locking device able to angularly lock the female and male parts when they are occupying the locking position, the angular locking device including a latch mounted radially movable on the back face of the locking plate and provided with a translating member accessible from the front face of the locking plate, the latch being intended to automatically engage in a limiting groove of an external edge of a bearing tooth;
   the female part including an abutment bottom for the male part limiting the engagement of the male part beyond the back face of the locking plate and having a rotational guiding surface between the male part and the female part in order to change from the insertion position to the locking position and conversely.

2. The removable system of claim 1, wherein the abutment bottom includes, as a rotational guiding surface, a circular stud of conical shape.

3. The removable system of claim 1, wherein the male part includes a number of bearing teeth equal to the number of retaining teeth of the female part.

4. The removable system of claim 1, wherein the bearing teeth of the male part and the retaining teeth of the female part are regularly angularly distributed.

5. The removable system of claim 1, wherein two neighboring retaining teeth of the female part together delimit a notch for passing a bearing tooth of the male part while two neighboring bearing teeth of the male part together delimit a hole for passing a retaining tooth of the female part.

6. The removable system of claim 5, wherein the angular width of a passing notch measured between two neighboring retaining teeth is equal to a value between 105 to 200% of the angular width measured for a bearing tooth.

7. The removable system of claim 6, wherein the external edge of the bearing teeth includes from each of its ends a bearing rail for the latch opening into the limiting groove.

8. The removable system of claim 1, wherein the latch is elastically stressed in extension by a spring member in its maximum extension position in such a way as to be gradually compressed when it is bearing against a rail of the external edge until it comes to automatically engage in the limiting groove.

9. The removable system of claim 1, wherein the latch is intended to automatically engage in the limiting groove of the external edge of the bearing tooth under the effect of its own weight.

10. The removable system of claim 1, wherein the latch is mounted to extend vertically plumb with the middle of a retaining tooth arranged in the locking plate.

11. Equipment including a device assembled with a support using a removable system of claim 1, including a male part equipping the support and a female part equipping the device.

12. The equipment of claim 11, wherein the device includes a casing with a back face provided with the female part of the removable system, the male part of which equips the support.

13. The equipment of claim 12, wherein the back face of the casing of the device is provided with the translating member of the locking latch, positioned near an upper edge of the casing.

14. Equipment of claim 11, wherein the device is a display screen of a medical endoscope.

* * * * *